United States Patent [19]

Yamaguchi et al.

[11] 4,445,379
[45] May 1, 1984

[54] APPARATUS FOR RECEIVING REFLECTED ULTRASONIC WAVES IN ULTRASONOGRAPHY

[75] Inventors: Keiki Yamaguchi; Yasuhito Takeuchi; Shinichi Sano; Takao Higashiizumi, all of Tokyo, Japan

[73] Assignee: Yokogawa Hokushin Electric Corporation, Tokyo, Japan

[21] Appl. No.: 362,736

[22] Filed: Mar. 29, 1982

[30] Foreign Application Priority Data

Mar. 4, 1982 [JP] Japan ................................. 57-34364

[51] Int. Cl.³ ............................................. G01N 29/04
[52] U.S. Cl. ..................................................... 73/631
[58] Field of Search ................. 73/631, 646, 648, 629, 73/620

[56] References Cited

U.S. PATENT DOCUMENTS 3,724,262 4/1973 Niklas ..................................... 73/631
4,016,750 4/1977 Green ..................................... 73/620
4,171,644 10/1979 Beller ..................................... 73/631

Primary Examiner—Anthony V. Ciarlante
Attorney, Agent, or Firm—Moonray Kojima

[57] ABSTRACT

An echo signal receiver receives higher level echo signals reflected from strong reflections sources or reflecting sources at areas close to a probe in a range of higher frequencies, and also receives lower level echo signals reflected from weak reflection sources or sources at areas remote from the probe in a range of low frequencies. The echo signal receiver comprises a multiple stage amplifier circuit for receiving the echo signal. Outputs from amplifiers at front stages are delivered via filters having higher frequency bands, and outputs from amplifiers at rear stages are delivered via filters having lower frequency bands. The outputs are passed through the filters and then combined into a single processed echo signal. As an alternative, a video signal derived from an echo signal which has passed through a circuit for varying frequency characteristics is compared with a reference voltage by a comparator, which produces an output that is rounded off by removing high frequency components in a low pass filter. The rounded off signal is fed to a circuit for varying frequency characteristics to control the same to change its frequency ban while the signal is being received. In another embodiment, the echo signal is received through a variable low cut filter having a cutoff frequency which can be increased or reduced dependent on the level of the echo signal.

12 Claims, 18 Drawing Figures

FIG.12
(a)
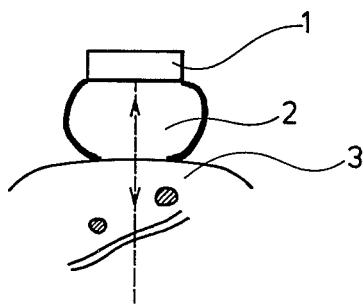
(b)
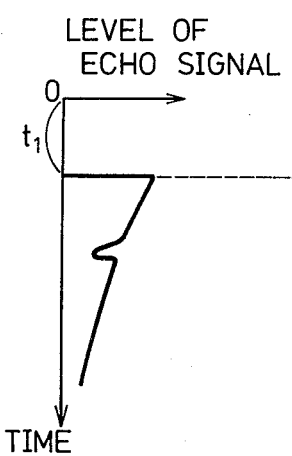
(c)
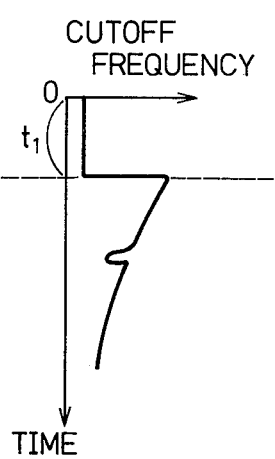
(d)
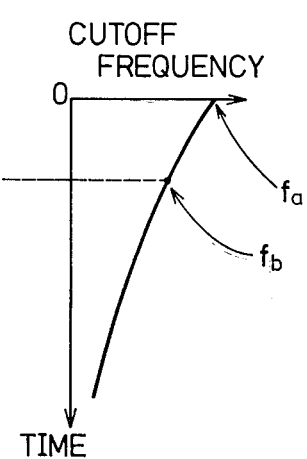

APPARATUS FOR RECEIVING REFLECTED ULTRASONIC WAVES IN ULTRASONOGRAPHY

BACKGROUND OF THE INVENTION

1. Field of the Invention

This invention relates to an apparatus for receiving reflected ultrasonic waves for use in ultrasonographic systems, and more particularly to such an apparatus employing a novel filter arrangement.

2. Description of the Prior Art

Ultrasonography utilizes ultrasonic waves to visualize various body structures for diagnosis. Ultrasonic waves, once they enter a test body, such as a living human body, undergo a relatively large degree of attenuation, to the extent that ultrasonic energy losses are not negligible for proper reception of reflected ultrasonic waves. In a form of ultrasonography, wherein echoes of ultrasonic pulses are received, an echo, reflected from the closest area and subjected to the least attenuation, while ultrasonic energy goes into the body and reflected back, is first received, and pulse echoes from more remote areas are successively received which are increasingly attenuated with increased distance from the receiver. To cope with this problem, there has been practiced in the art a system known as the TGC system, wherein the gain of an echo signal receiver is first reduced and progressively increased as time elapses, from the time the first ultrasonic pulses are emitted, while reflected ultrasonic waves are being received.

However, the known TGC echo reception system is disadvantageous in that it cannot compensate for energy dispersion in the medium, such as the human body. More specifically, weak echo signals, that is, echo signals which are of a low level or are reflected from deeper areas, cannot fully be received simply by increasing the gain of an amplifier. It is preferable that areas, which reflect weak ultrasonic waves, as viewed from a probe, be observed with lower frequencies, taking into consideration, reflective characteristics of such areas and dispersion in the medium being tested, which cause greater energy losses at higher frequencies.

One known system designed to meet such requirements, is for example, disclosed in U.S. Pat. No. 4,016,750. In this system, reflected ultrasonic waves are received by a receiver having a filter with its central frequency fo progressively lowered as the receiver receives echo signals from reflecting areas increasingly remote, or the time required to receive echo signals becomes increasingly longer. This system is effective for use with an object constituted by reflecting areas or sources that send back echoes which can be received at levels which become lower as the distance to the reflecting sources is greater. However, actual objects or bodies to be tested contain various tissues which have different attentuation characteristics, dispersing properties, and reflecting properties. Thus, this reception system is not considered effective for use with such objects which provide no constant or linear relationship between the distance to reflecting areas and the level at which reflected ultrasonic waves are received, such as the living human body.

The difficulties with the prior system can be shown with reference to FIG. 1, which depicts an ultrasonographic system, wherein ultrasonic waves are emitted into and received from a test body 3 by a probe 1 with a transitional device, such as water bag 2, interposed therebetween. In this system, the probe 1 sends ultrasonic waves into the body 3, and parts of such body as scanned with reflect back the ultrasonic waves, such as by echo signals, and probe 1 will receive such echo signals. With such an ultrasonographic system, the probe 1 tends to receive lower components of ultrasonic waves, as reflected from the test body 3, when the central frequency of the filter is lowered, as echo reflecting areas become deeper and further from the probe. Accordingly, no good display quality is available since the lower the cutoff frequency, the better the quality of displayed images. In other words, in such a system for ultrasonic echo imaging, the system receives a much lower frequency than when a water bag is not used and actual echo from the object human being body comes back. This is due to the system center frequency being tuned down monotonically at a predetermined rate without any regard to the actual situation of the echo sources. Thus, only poor quality sonic image is available, since in general, the more the lower frequency component is suppressed, the better the image quality (especially in resolution and detailed texture) is to be obtained.

SUMMARY OF THE INVENTION

Accordingly, an object of the invention is to provide an apparatus for receiving ultrasonic waves for use in ultrasonography, to obtain more precise sectional images of a test body by receiving echo signals from reflecting areas in a test body, through a filter having a frequency band which is variable depending on the levels of the received echo signals.

Another object of the present invention is to provide an apparatus for receiving reflected ultrasonic waves for use in ultrasonography, wherein the apparatus is capable of scanning areas for reflecting in a range varying from high level ultrasonic echoes to low level ultrasonic echoes, and capable of displaying the picked up reflections as B-scan echograms suitable for use in diagnosis.

Another object is to provide an echo receiver which can successfully accept echo signals over an increased dynamic range of target intensity, i.e. from highest level echo sources down to the lowest level echo sources, so as to construct images having equalized quality of texture details over a range of various echo sources.

According to this invention, a receiver circuit has frequency characteristics which are variable depending on the levels of received echo signals, and extracts such echo signals. High level echo signals are received in a high frequency band, and low level ehco signals are received in a low frequency band or a frequency band which extends into the low frequencies.

The foregoing objects, features, and advantages will become more apparent from the following description taken together with the drawings, wherein preferred embodiments are depicted as illustrative of the principles of the invention.

BRIEF DESCRIPTION OF DRAWINGS

FIG. 12(a) is a diagram showing an ultrasonographic system.

FIGS. 12(b) and 12(c) depict graphs illustrative of the operation of a filter according to the invention.

FIG. 12(d) is a graph illustrating the operation of a prior art filter.

DETAILED DESCRIPTION OF PREFERRED EMBODIMENTS

Figure 1:
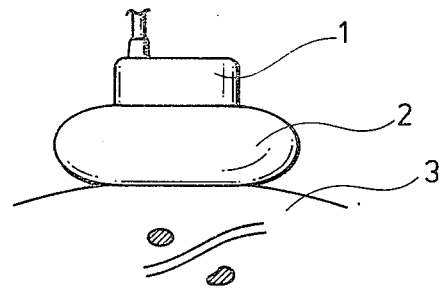
FIG. 1 is a schematic diagram showing an ultrasonographic system.
Figure 2:
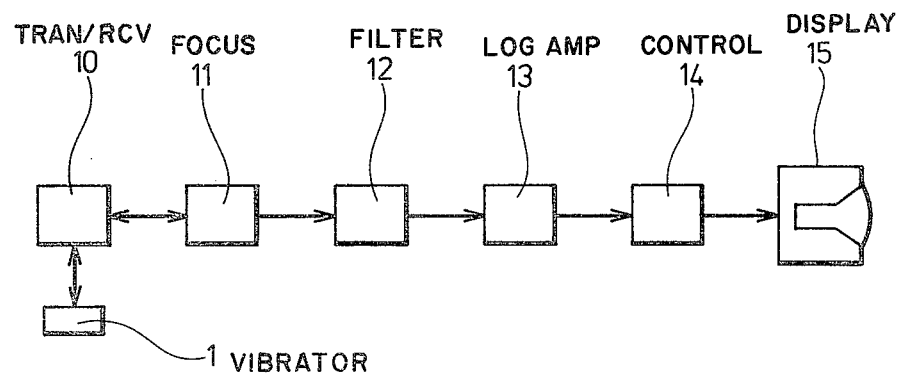
FIG. 2 is a block diagram of an ultrasonographic system, including an echo signal receiver according to the invention.

As shown in FIG. 2, an ultrasonographic system comprises a vibrator unit 1 having an array of ultrasonic vibrators, an ultrasonic transmitter and receiver 10, an electronic focusing circuit 11, a filter 12, a logarithmic amplifier 13, a controller 14, and a display unit 15 having a display device, for example, a cathode ray tube (CRT). Transmitter and receiver 10 serves to drive or energize the array of ultrasonic vibrators individually and receive echo signals, as received and converted into electrical signals by vibrator unit or probe 1. Electronic focusing circuit 11 serves to focus a beam of ultrasonic waves emitted from and received by probe 1. Electronic focusing circuit 11 energizes transmitter and receiver 10, with a time delay, for converging an ultrasonic beam, and delays echo signals from the array of ultrasonic vibrators so as to combine such delayed echo signals into a single echo signal. The echo signal thus formed is processed by filter 12, then logarithmically compressed by logarithmic amplifier 13, and displayed as a visible image on display unit 15 under the control of controller 14. With this arrangement, a beam of ultrasonic energies can be emitted from and received, as reflected, by probe 1, while at the same time being scanned in a direction normal to the direction of travel of the ultrasonic beam, and the received ultrasonic echoes can be displayed on display unit 15 as a B-scan echogram image.

Figure 3:
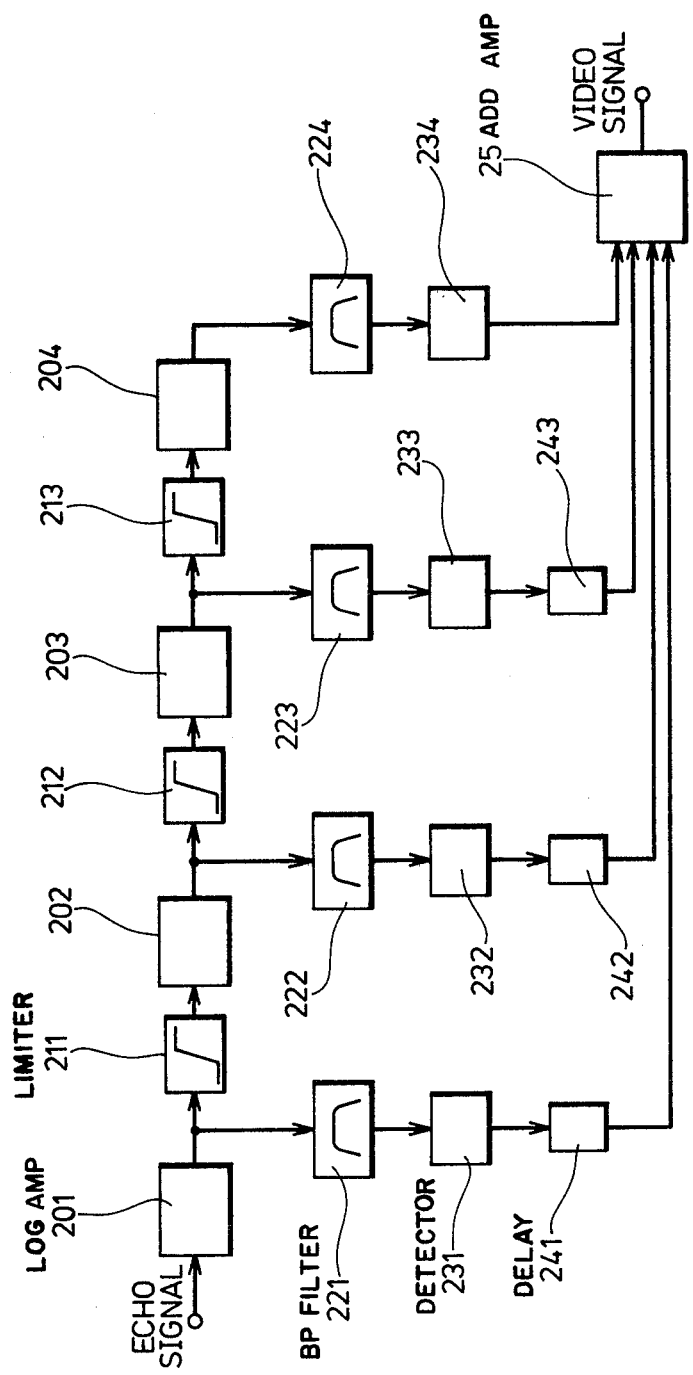
FIG. 3 is a block diagram of a filter illustrative of an embodiment of the invention, and usable for example in the embodiment of FIG. 2.

FIG. 3 shows filter 12 in more detail. With filter 12 thus constructed, logarithmic amplifier 13 can be dispensed with. As depicted, filter 12 includes logarithmic amplifiers 201 . . . 204, limiters 211 . . . 213, bandpass filters 221 . . . 224 having different central frequencies and frequency bands that can be transmitted detectors 231 . . . 234, delay lines 241 . . . 243, and an adder amplifier 25. First stage logarithmic amplifier 201 receives echo signals supplied from probe 1 and logarithmically amplifies the received echo signals at a given amplification factor. An output from first stage logarithmic amplifier 201 is delivered to first bandpass filter 221 and to the next logarithmic amplifier 202 through limiter 211. Logarithmic amplifier 202 produces an output which is fed to second bandpass filter 222 and to the next logarithmic amplifier 203 via limiter 212. Likewise, logarithmic amplifier 203 generates an output which is transmitted to third bandpass filter 223 and to the final stage logarithmic amplifier 204 through limiter 213. An output from the final stage logarithmic amplifier 204 is supplied to fourth bandpass filter 224. Iogarithmic amplifiers 202 . . . 204 and associated limiters 211 . . . 213 jointly constitute sequential saturation type logarithmic amplifier circuits, which form a main section of a receiving system. First stage logarithmic amplifier 201 processes an echo signal of a maximum level, and final stage logarithmic amplifier 204 processes an echo signal of a minimum level. Bandpass filters 221 . . . 224 have central frequencies $f_1$, $f_2$, $f_3$ and $f_4$ which are selected to satsify the relationship of $f_1 > f_2 > f_3 > f_4$ and also have respective bandwidths which are suitably selected. Alternating current signals which have passed through bandpass filters 221 . . . 224 are fed to detectors 231 . . . 234, respectively, for detection therein. Outputs from detectors 231 . . . 234 are added by adder amplifier 25 and transmitted as an output video signal. The outputs of the first to third detectors 231 . . . 233 are led to adder amplifier 25 respectively via delay lines 241 . . . 243, for delaying such outputs to correct time delays the outputs have with respect to the output from final stage detector 234. Time delays which are given by delay lines 241 . . . 243 are the larger, the closer delay lines 241 . . . 243 are to the first stage. The time delays the delay lines produce and time delays derived from the bandwidths of the bandpass filters, are determined so that the four signals supplied to the adder amplifier 25 will be added together at the same time.

In order to receive reflected ultrasonic waves of various frequencies distributed over a wide range from a variety of reflecting areas or sources, it is desirable that probe 1 be driven by a signal having a stepped waveform (which may be a rising edge of a triangle wave) to transmit ultrasonic waves that are as impulse shaped as possible. The circuit for receiving reflected waves should preferably be of a wide frequency range. At the least, first logarithmic amplifier 201 should be of a wide frequency range. Logarithmic amplifier 201 may be preceded by a preamplifier, which should also have a sufficiently wide frequency range.

Figure 4:
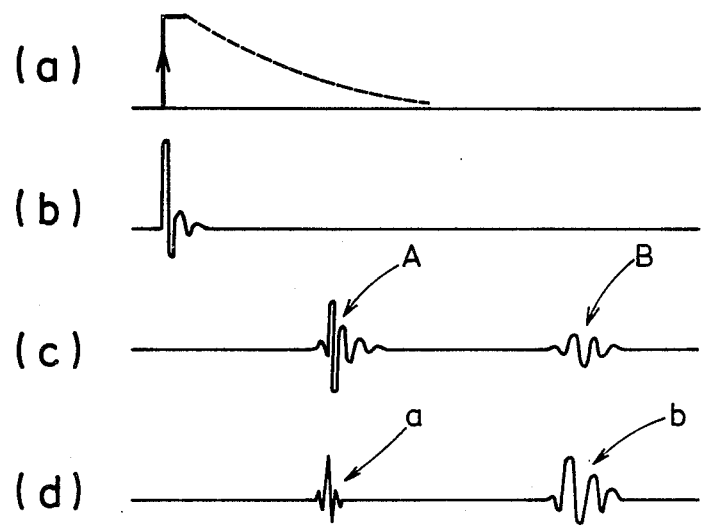
FIGS. 4(a)-(d) are diagrams showing waveforms of a drive signal and echo signals, such as used in the embodiment of FIG. 3.

Operation of the filter of FIG. 3, thus constructed, for receiving reflected ultrasonic waves is as follows: Probe 1 is energized with a stepped drive signal, as shown in FIG. 4(a), to emit an ultrasonic wave, as shown in FIG. 4(b) into a test body. Such an impulse ultrasonic wave is partly reflected by an interface between different tissues or mediums in the test body, and a reflected ultrasonic wave or an echo signal is received by probe 1. Such a received echo signal is illustrated in FIG. 4(c).

The echo signal comprises a high level echo signal component A (which has a relatively wide frequency spectrum) reflected from a strong reflection source or a reflecting source located at an area closer in distance to probe 1, and a low level echo signal B (which mainly has a spectrum of lower frequencies) reflected from a weak reflection source or a reflecting source located at an area more remote in distance from probe 1. The echo signal is sequentially amplified by the successive saturation type logarithmic amplifier circuit.

Since the reflected wave A mainly comprises higher frequency components, it passes through the former bandpass filter which has a frequency band including such frequency components. The subsequent logarithmic amplifiers, upon amplifying the echo signal A, receive a saturated signal which is given by limiting the echo signal, and hence produce predetermined saturated outputs irrespective of the frequency characteristics that the amplifiers may have. The reflected wave B comprising lower frequencies components passes through the latter bandpass filter which has a frequency band including the lower frequencies. The bandpass filters which are supplied with outputs from the former stages cut off the reflected wave B because of different frequency bands. Even when the reflected wave B contains a frequency component which passes through these bandpass filters, such a frequency signal is of such a low energy level that it will not affect detector outputs.

As shown in FIG. 4(d), the echo signal component A is changed into a high frequency signal a by the corresponding bandpass filter, and the echo signal component B is changed into a low frequency signal b by the corresponding bandpass filter. These signals a and b are detected by the corresponding detectors. Where the detectors are accompanied by delay lines, the signals are delayed thereby. The signals are then added together by the adder amplifier 25, which produces a combined output video signal that is logarithmically compressed.

Thus, a lower level echo signal is received in a limited bandwidth of lower frequencies, and a higher level echo signal, reflected from a source which reflects an ultrasonic wave at a higher level, is received in a range of higher frequencies which are capable of indicating minute structures of the reflecting source within its own frequency bandwidth.

While in the illustrative embodiment of FIG. 3, the number of amplifier stages is four, it may be increased or reduced as desired. For some purposes, it is practically acceptable to merely add the outputs from the detectors without delaying the outputs as described with reference to the illustrated embodiment.

Figure 5:
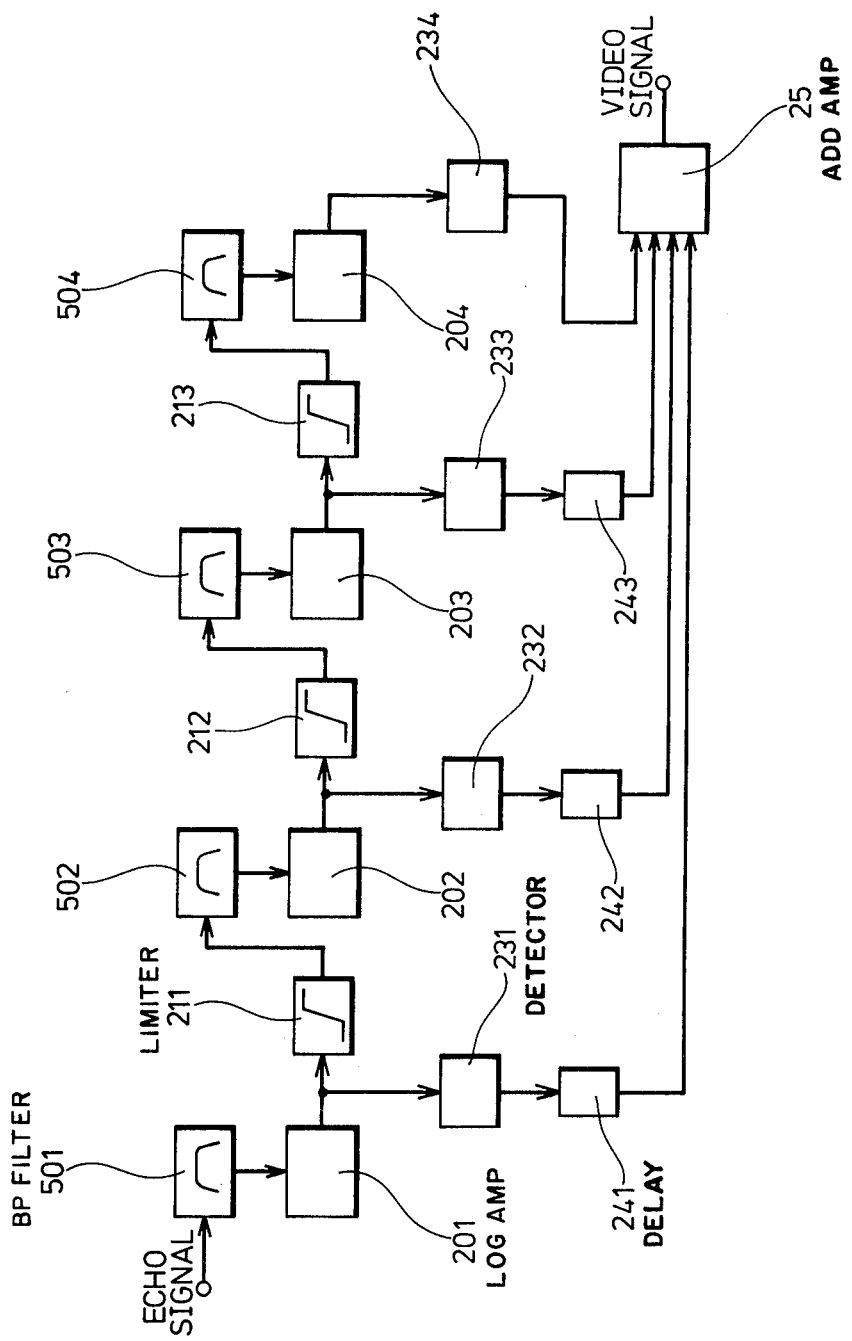
FIG. 5 is a block diagram of a filter illustrative of another embodiment of the invention.

FIG. 5 shows a filter according to another embodiment. It differs from the filter shown in FIG. 3, in that, the bandwidth becomes smaller at the rear stages. More specifically, logarithmic amplifiers 201 . . . 204 are preceded by bandpass filters 501–504 having different frequency characteristics, and produce outputs that directly go to detectors 231 . . . 234, respectively.

Bandpass filters 501 . . . 504 have frequency band widths $F_1$, $F_2$, $F_3$ and $F_4$ which are progressively smaller towards rear stages, such that, each bandpass filter has a frequency selection characteristic which is included in those of former bandpass filters. More specifically, the first stage logarithmic amplifier produces an output which is subjected to the frequency characteristic of filter 501. Outputs from the second stage and subsequent amplifiers are subjected to the frequency characteristics of former filters, as multiplied by those of the filters receiving the outputs. Thus, the final stage amplifier produces an output which undergoes all of the characteristics of filters 501 . . . 504, which are multiplied together.

With the arrangement shown in FIG. 5, an apparatus for receiving reflected waves according to the present invention includes successively cascaded filters for effective reception of echo signals.

Bandpass filters 501 . . . 504 show in FIG. 5 may partly or wholly be replaced with low pass or high pass filters. Delay lines 241 . . . 243 may be dispensed with for some applications.

Figure 6:
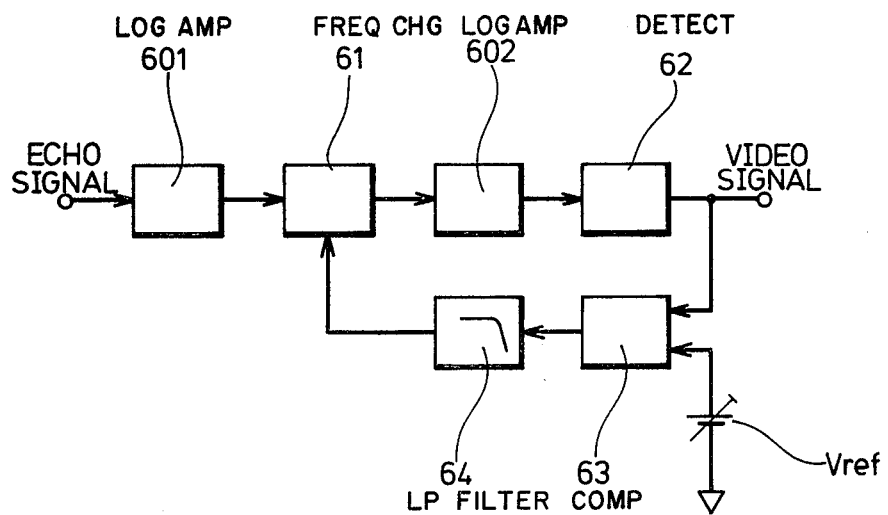
FIG. 6 is a block diagram of a filter illustrative of still another embodiment of the invention.

FIG. 6 illustrates a receiver system according to still another embodiment of the invention, for determining the level of an echo signal, and for changing the impulse response of the receiver system in response to the determined level for reception of echo signals. The receiver system shown in FIG. 6 comprises logarithmic amplifiers 601, 602, a circuit 61 for changing frequency characteristics, a detector 62, a comparator 63, and a low pass filter 64.

In operation, an echo signal is supplied to first stage logarithmic amplifier 601, which amplifies the received echo signal. Then, an amplified signal from logarithmic amplifier 601 is fed via circuit 61 to logarithmic amplifier 602 and detector 62 for amplification and detection, thereby producing a video signal containing a d-c component. The video signal is compared with a reference value, that is, a semi-adjustable reference voltage $V_{ref}$, in comparator 63. An output from comparator 63 is caused to pass through low pass filter 64 to remove high frequency components from the comparator output, or to round off the comparator output. Low pass filter 64 transmits its output to circuit 61 for feedback control. Circuit 61, for changing frequency characteristics, is responsive to a control voltage supplied from low pass filter 64, for varying frequency ranges for signal processing. Low pass filter 64 may also be referred to as an integrator since a 1st order simple low pass filter is conventially called an integrator.

Figure 7:
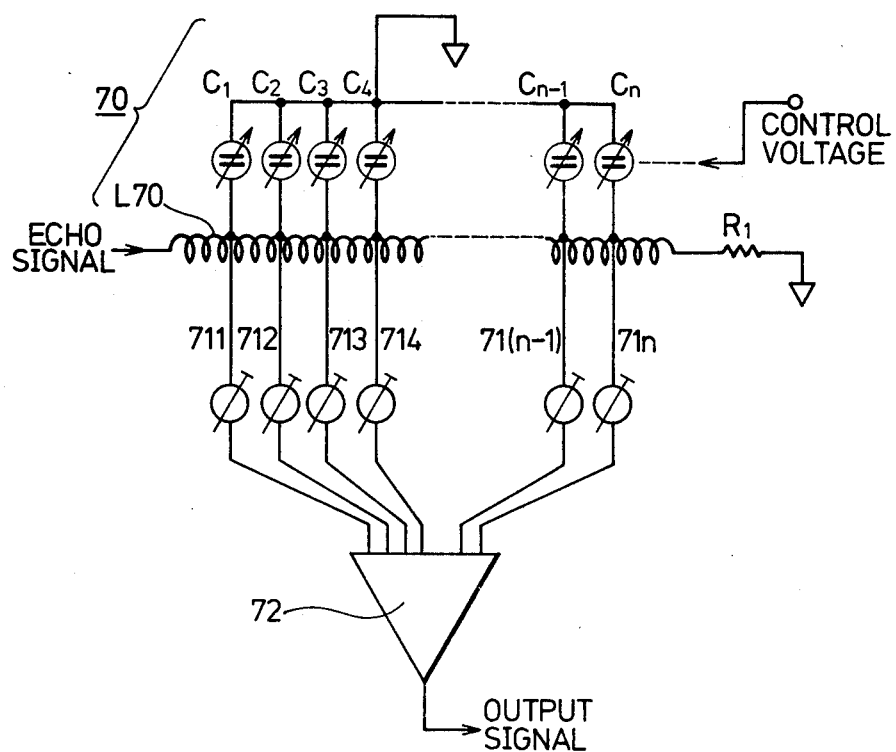
FIG. 7 is a circuit diagram of a circuit, such as shown in FIG. 6, for changing frequency characteristics.

FIG. 7 shows an illustrative detailed circuit, which may be used as circuit 61 in FIG. 6. The circuit includes tapped delay lines 70, variable coefficient couplers 711 . . . 71n connected respectively to delay lines 70, and an adder amplifier 72 for adding outputs from the variable coefficient coupler. The circuit arrangement is known as a transversal signal processing circuit. Delay lines 70 comprise a coil L70 having a plurality of taps, and a plurality of variable capacitors $C_1$ . . . $C_n$ having one end thereof connected to a load resistor $R_1$ and coupled respectively between the taps on the coil and a common line. The capacitors have capacitances which are variable depending on an external control voltage. When the electrostatic capacities of the variable capacitors are varied, the speeds at which signals are delivered over the delay lines are varied, to thereby change a unit sampling rate on a time basis for processing signals. With this arrangement, therefore, the scale factor of the frequency characteristic or of the impulse response of the overall circuit construction can be varied.

Figure 8:
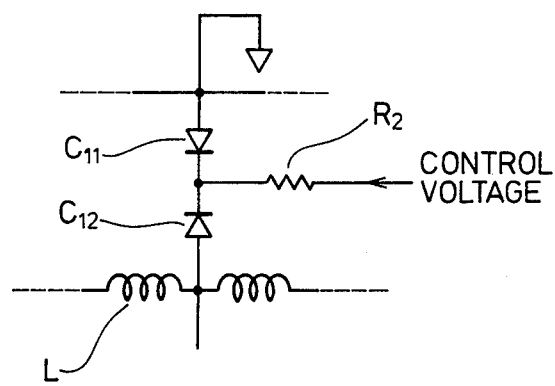
FIG. 8 is a circuit diagram of a variable capacitor, such as shown in FIG. 7.

As shown in FIG. 8, each of the variable capacitors $C_1$ . . . $C_n$ of FIG. 7 may preferably comprise a pair of variable capacitance diodes $C_{11}$ and $C_{12}$ coupled in an anti-series connection, and a resistor $R_2$ having one end thereof connected to the junction between the diodes. The resistor $R_2$ preferably has a relatively high resistance. The capacitances of the variable capacitance diodes can be changed by applying a control voltage to the other end of resistor $R_2$, without requiring a bypass for a signal current flowing through the diodes. The anti-series connection of the diodes is of advantage in preventing interference between a signal to be processed and a control voltage especially for high speed control.

For transversal signal processing, there is no need to use all of the taps on variable delay lines 70 (see FIG. 7) and those in which the coefficients can be approximated to zero may be negligible. The present invention is not limited to the illustrated transversal signal processing circuit. For example, signal processing on a series of sampled signals on a time base can be effected by ordinary digital filters. With such an alternative, the scale factor of the impulse response or of the frequency characteristic can freely be adjusted by changing a sampling frequency.

In any arrangement, the comparator (see FIG. 6) may be an ordinary comparator having a nominal infinite gain, or an ordinary differential amplifier having a suitable finite gain.

The low pass filter 64 (see FIG. 6) may comprise an integrator. The feedback system should have a response time which is sufficiently slower than the period of one vibration of the waveform of a reflected wave. However, if the response time were far slower than a unit of resolution power on a time base, or the direction of an ultrasonic beam (z-axis), of the overall transmission and reception system of the ultrasonographic apparatus, the quality of images displayed would be likely to change unexpectedly. The time delay should be selected so as to be equal to a unit of resolving power.

The arrangement of FIG. 6 can be employed for the same results as that obtained through use of the arrangement of FIG. 3. More specifically, a high-level reflected wave signal from a source which reflects echoes of higher levels, or from a source at an area close to the probe, is processed only to extract signal components having higher frequencies. In the ultrasonographic system, the higher the frequencies of signals, the greater the resolution power, and the better the minute structures of the medium that can be seen on the display unit. On the other hand, a lower level echo signal reflected from a source which sends back reflections of lower levels, or from a source remoter from the probe, is processed so as to emphasize a lower frequency range that agrees to a frequency spectrum the echo signal has, for reception with an improved signal to noise ratio.

Figure 9:
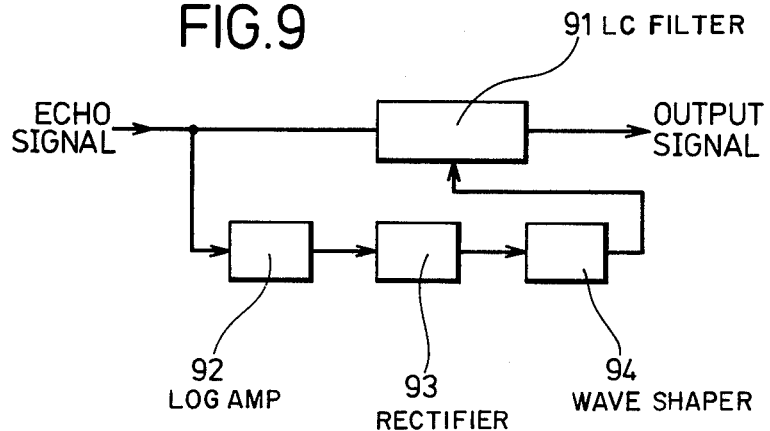
FIG. 9 is a block diagram of a filter illustrative of still further embodiment of the invention.

FIG. 9 illustrates a filter according to still another embodiment. The filter shows a variable low cutfilter 91 and a logarithmic amplifier 92, which are supplied with an echo signal. An output signal from logarithmic amplifier 92 is fed to a peak rectifier 93 which detects a peak of the signal received. The detected peak signal is supplied to a waveform shaping circuit 94 wherein high frequency components are removed from the signal and the latter is shaped. An output signal from waveform shaping circuit 94 is supplied to variable lowcut filter 91 as a control voltage for controlling a cutoff frequency. Waveform shaping circuit 94 comprises a low pass filter having an appropriate cutoff frequency, a nonlinear circuit with its amplification factor being variable depending on the amplitude of a signal, and others.

Variable low cut filter 91 has its cutoff frequency variable depending on the control voltage applied by waveform shaping circuit 94. When control voltage is higher, the cutoff frequency becomes higher, and when the control voltage is lower, the cutoff frequency becomes lower. To put this another way, in contrast to the FIG. 6 embodiment, FIG. 9 illustrates a forward feed control scheme, wherein the echo signal is branched at the top or suitable intermediate stage to a couple of routes, one being a main route through variable filter 91, and the other being a special signal conditioning route comprising logarithmic amplifier 92, peak detector (rectifier) 93, and a waveform shaping circuit 94.

The waveform shaping circuit typically is constructed by a suitable smoothing filter incorporated with optional non-linear processing circuit.

The latter route is similar to a conventional echo receiver to obtain echo intensity video signal; however, in this embodiment, the output is utilized to modify the frequency selective Characteristics of the variable filter 91.

According to a general concept of this invention, the echo intensity signal from the latter route tunes "up" the filter when intense echo signal is coming in, and tunes "down" the filter when the echo signal is faint. The scheme is substantially completely of feed forward configuration, so that, advantageously, it is completely free from possible hunting or instability due to inadequate feedback parameter design, such as may be the case of the feedback scheme of FIG. 6, for example.

The variable filter 91 typically is a center frequency variable bandpass filter; however, insome cases, lower cutoff frequency variable, higher cutoff frequency finite band pass filter may be utilized. In such case, lower cutoff frequency is increased for intense echo, while being decreased for faint echo.

Figure 10:
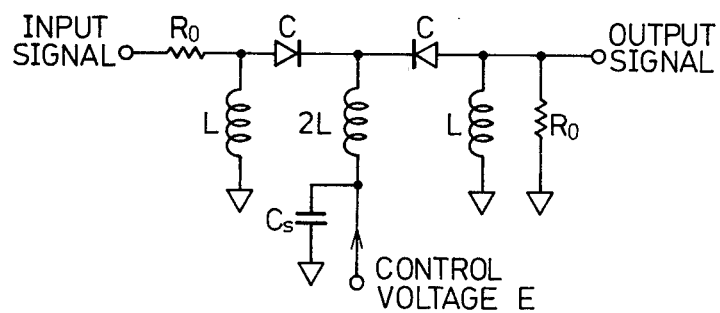
FIG. 10 is a circuit diagram of a variable low-cut filter, such as usable in FIG. 9.
Figure 11:
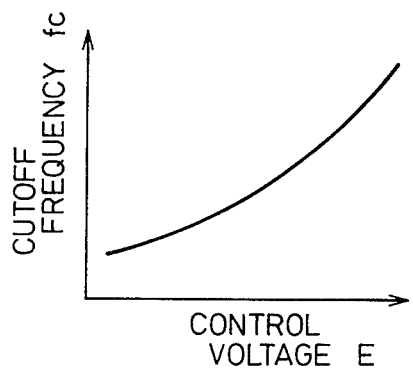
FIG. 11 is a graph showing characteristic of the low-cut filter, such as shown in FIG. 10.

Variable low cut filter 91 may be of various constructions. One preferred arrangement of such filter is shown in FIG. 10. The circuit of FIG. 10 includes variable capacitors C and is in the form of a constant K filter, which is an eighth variable low cut filter with its low cutoff frequency being variable. An impedance matching resistor $R_o$ is selected so as to satisfy the following equation:

$$R_o = \sqrt{\frac{L}{C_c}}$$

wherein $C_c$ is the central value in a range in which the capacitances of the variable capacitors are variable. A control voltage E is applied from a waveform shaping circuit via an inductor to the variable capacitors C. One end of the inductor 2L to which the control voltage is applied is grounded through a capacitor Cs. The capacitances of the variable capacitors C vary depending on changes in the control voltage. The cutoff frequency fc of the filter is variable according to the following equation, depending on the control voltage as shown in FIG. 11.

$$fc = \frac{1}{2\pi \sqrt{LC}}$$

The filter 91 (see FIG. 9) may be combined with a suitable high cut filter, jointly providing a bandpass filter having its cut off frequency variable in the manner abovedescribed.

Operation of the arrangement shown in FIG. 10, will be described with reference to the ultrosonographic systems shown in FIG. 12(a), wherein a beam of ultrasonic energies is emitted from and received as reflected, by a probe 1, with a water bag transitional device 2 interposed between the probe 1 and a test body 3, which is being subjected to ultrasonographic diagnosis. For the sake of brevity, a beam of ultrasonic waves is shown by a single dotted line. The level of an echo signal which is received is shown in FIG. 12(b). Ultrasonic waves transmitted from probe 1 are reflected successively from a surface of test body 3 and internal areas thereof. Upon elapse of an interval of time $t_1$ from the time at which the ultrasonic beam is emitted, a strong echo wave is reflected from the surface of the body 3.

Then, reflected ultrasonic waves are sent back from the different tissue interfaces at varying depths in body 3, and received by probe 1. The intensities of reflected ultrasonic energies sent back from acoustically discontinuances in interfaces with the body 3, are not a simple function of the depth from the surface of body 3, but, are dependent on the acoustic characteristics of the tissues of body 3.

Under actual conditions, ultrasonic waves of more intensive energies are frequently reflected back from deeper areas than more shallow areas. Such a reflected ultrasonic wave is converted into a corresponding electrical signal (voltage signal), which is fed to the variable low cut filter 91 (see FIG. 9) as a signal having a level which is variable with time as shown in FIG. 12(b). At the same time, a control voltage is generated by logarithmic amplifier 92, peak rectifier 93, and waveform shaping circuit 94, and corresponds to the level of the echo signal as illustrated in FIG. 12(b). Variable low cut filter 91 which is controlled by control voltage thus produced, has its cutoff frequency variable in timed relation to the echo signal level shown in FIG. 12(b). As is apparent from the FIGS. 12(b) and 12(c), the cutoff frequency becomes higher when the echo signal is at a higher level, allowing filter 91 to act as a filter for passing higher frequencies. Conversely, when the echo signal is at a lower level, the cutoff frequency becomes lower, and filter 91 serves as a filter having a frequency bandwidth extending into lower frequencies. Signals which have passed through filter 91 with its cutoff frequency being variable depending on the echo signal level are better indicative of a distribution of acoustic characteristics in body 3. An echogram image obtained on the basis of such signals is of good quality displaying a sectional image of body 3 with high fidelity.

FIG. 12(d) is illustrative of the cutoff frequency of a conventional filter, which becomes lower as echo signals are reflected from deeper areas. With prior filters, the cutoff frequency was reduced from an initial value fa to a value fb upon elapse of time interval $t_1$ which corresponds to the depth from the surface of the test body, irrespective of the fact that substantially no loss of ultrasonic energies is caused by water bag 2. The cutoff frequency continues to become reduced without regard to subsequent variations in energy loss. Signals having passed through such a filter differ considerably from actual echo signals reflected from sectional planes in the testbody. Hence, the sectional images, as displayed, appear different from the actual structures of the test body, which are under ultrasonic examination.

With the present invention, as described above, an apparatus for receiving reflected ultrasonic waves, receives echo signals, while removing as low frequency components as possible from a frequency spectrum of the received echo signal and produces images on higher frequency components only, for better image quality. This advantageous result has experimentally been confirmed.

Removal of low frequency components should be effected in a range wherein the signal-to-noise ratio does not adversely affect the images displayed. Such removal should be performed in direct response to the level of an echo signal which is about to arrive fro displaying images of good quality. Thus, according to the present invention, low frequency components to be removed are determined in response to the levels of echo signals for thereby obtaining, without failure, quality images.

Furthermore, the apparatus of this invention can produce B-scan images which are more uniform and precise, and less depth dependent, than images which have been produced by prior art receivers relying solely on the TGC type echo reception system, that is, a system wherein only the gain of the receiver is controlled in response to the depth of reflecting surfaces (which corresponds to the interval of time required for reflected waves to be sent back).

The inventive apparatus, advantageously, can also be combined for use with known TGC echo reception systems.

The invention employs a high frequency range, to process reflected ultrasonic waves of intensive levels indicating minute structures of an object being studied (that is, reflected waves of high frequency components indicative mainly of minute structures), which would be contracted and could not be seen even with logarithmic compression, as effected in conventional TGC systems. The apparatus of this invention, can create B-scan images containing substantial information of minute structures of the object being studied, and displaying everything from bright spots to dark spots.

With the system as disclosed in U.S. Pat. No. 4,016,750, an object having a hole which passes sound and does not greatly attenuate sound energy is visualized in a manner completely different from an object having no such hole, since the disclosed system relies on linearly corrected frequency characteristics. To cope with such a problem, signals should be processed on the basis of dispersion which ultrasonic waves undergo in actual situations. The dispersion to which ultrasonic waves are subjected in an object can be better understood when taking into account the amount of attenuation the ultrasonic waves have suffered, or the intensity of reflected echoes sent back from the object. The invention can produce more substantive sectional images irrespective of whether an object or test body has a hole or not in an area which is being subjected to ultrasonographic diagnosis.

Although certain preferred embodiments have been shown and described in detail, it should be understood that various changes and modifications may be made therein without departing from the scope of the appended claims.

What is claimed is:

1. In an ultrasonographic system comprising means for emitting ultrasonic waves into a test body, said test body or parts thereof reflecting said ultrasonic waves as echo signals, apparatus for receiving said reflected echo signals, and means for displaying said echo signals as B-scan echograms; the improvement comprising said apparatus comprising a filter for processing said echo signals in response to instantaneous levels of said echo signals, so as to utilize higher frequency components of said echo signal when the instantaneous level of said echo signal is high, and so as to utilize lower frequency components of said echo signal when the instantaneous level of said echo signal is low, and also comprising means to detect said instantaneous level of said echo signal and to control said filter effectively on its partial or total contribution to said processing of of said echo signals.

2. In an ultrasonographic system comprising means for emitting ultrasonic waves into a test body, said test body or parts thereof reflecting said ultrasonic waves as echo signals, apparatus for receiving said reflected echo signals, and means for displaying said echo signals as B-scan echograms; the improvement comprising said apparatus comprising a filter for processing said echo signals in response to instantaneous levels of said echo signals; wherein said filter is capable of receiving said echo signal in a range of higher frequencies when the echo signal has a higher level, and in a range of lower frequencies when the echo signal has a lower level; and where said filter comprises an input terminal for receiving said echo signal, a detector for detecting said echo signal, an amplifier connected between said input terminal and said detector and having at least one circuit for varying frequency characteristics, at least one source of reference voltage, and a comparator or differential amplifier for receiving an output from said detector and a reference voltage from said source, wherein said echo signal is received while characteristics of said at least one circuit for varying frequency characteristics are changeable depending on an output from said comparator.

3. The apparatus of claim 2, wherein said filter further comprises a low-pass filter for smoothing an output from said comparator and feeding a smoothed output back to a characteristics control terminal of said at least one circuit for varying frequency characteristics.

4. The apparatus of claim 3, wherein said comparator, said low pass filter, and said at least one circuit for varying frequency characteristics jointly constitute a feedback control system, having response characteristics including a response time which is substantially equal to a resolving power on a time basis of said ultrasonographic system.

5. The apparatus of claim 2, wherein said at least one circuit for varying frequency characteristics, has an echo signal amplifying rate which is variable depending on an external control voltage.

6. The apparatus of claim 5, wherein said at least one circuit for varying frequency characteristics, comprises a ladder type delay line network, including an inductor having a plurality of taps, a common line, a plurality of variable capacitance diodes connected respectively between said taps and said common line, said external control voltage being applicable to said variable capacitance diodes for providing variable time delays, a plurality of variable coefficient couplers corrected, respectively, to, or connected to selected ones of, said taps, and an adder amplifier for adding and amplifying outputs from said variable coefficient couplers.

7. In an ultrasonic system comprising means for emitting ultrasonic waves into a test body, said test body or parts thereof reflecting said ultrasonic waves as echo signals, apparatus for receiving said reflected echo signals, and means for displaying said echo signals as B-scan echograms; the improvement comprising said apparatus comprising a filter for processing said echo signals in response to instantaneous levels of said echo signals; wherein said filter is capable of receiving said echo signals in a range of higher frequencies when the echo signal has a higher level, and in a range of lower frequencies when the echo signals has a lower level; and wherein said filter comprises a successive saturation type logarithmic amplifier circuit including a plurality of series connected logarithmic amplifiers and a plurality of limiters preceding said logarithmic amplifiers, respectively, for limiting the amplitude of input signals, a plurality of bandpass filters connected respectively to outputs of said logarithmic amplifiers and having mutually different characteristics, a plurality of detectors for detecting outputs from said bandpass filters, and an adder amplifier for adding and amplifying outputs from said detectors into a logarithmically compressed video signal.

8. In an ultrasonographic systems comprising means for emitting ultrasonic waves into a test body, said test body or parts thereof reflecting said ultrasonic waves as echo signals, apparatus for receiving said reflected echo signals, and means for displaying said echo signals as B-scan echograms; the improvement comprising said apparatus comprising a filter for processing said echo signals in response to instantaneous levels of said echo signals; wherein said filter is capable of receiving said echo signal in a range of higher frequencies when the echo signal has a higher level, and in a range of lower frequencies when the echo signal has a lower level; and wherein said filter comprises a successive saturation type logarithmic amplifier including a plurality of series connected logarithmic amplifiers, a plurality of filters preceding said logarithmic amplifiers, respectively, and having different frequency bands, and a plurality of limiters preceding said logarithmic amplifiers, respectively, for limiting the amplitudes of input signals, a plurality of detectors for detecting outputs from said logarithmic amplifiers, respectivey, and an adder amplifier for adding and amplifying outputs from said detectors into a logarithmically compressed video signal.

9. In an ultrasonographic system comprising means for emitting ultrasonic waves into a test body, said test body or parts thereof reflecting said ultrasonic waves as echo signals, apparatus for receiving said reflected echo signals, and means for displaying said echo signals as B-scan echograms; the improvement comprising said apparatus comprising a filter for processing said echo signals in response to instantaneous levels of said echo signals; wherein said filter comprises a variable filter having a cutoff frequency which is variable depending on the level of the echo signal.

10. The apparatus of claim 9, wherein said variable filter comprises a low cut filter or a bandpass filter.

11. The apparatus of claim 9, wherein said variable filter is capable of increasing its cutoff frequency when the level of said echo signal received, is relatively high, and of reducing its cutoff frequency when the level of said echo signal received, is relatively low.

12. In an ultrasonographic system comprising means for emitting ultrasonic waves into a test body, said test body or parts thereof reflecting said ultrasonic waves as echo signals, apparatus for receiving said reflected echo signals, and means for displaying said echo signals as B-scan echograms; the improvement comprising said apparatus comprising a filter for processing said echo signals in response to instantaneous levels of said echo signals; wherein said filter comprises a variable low cut filter or band pass filter, for receiving said echo signal, a logarithmic amplifier for logarithmically amplifying said echo signal, and means for producing a voltage signal corresponding to a peak value of an output signal from said logarithmic amplifier, said variable low cut filter having a cutoff frequency controllable by the output voltage of said means for producing a voltage signal.

* * * * *